(12) United States Patent
El-Ghannam

(10) Patent No.: US 7,223,414 B1
(45) Date of Patent: May 29, 2007

(54) SILICA-CALCIUM PHOSPHATE BIOACTIVE COMPOSITE FOR IMPROVED SYNTHETIC GRAFT RESORBABILITY AND TISSUE REGENERATION

(76) Inventor: Ahmed El-Ghannam, 3306 Monte Vista Rd., Apt. D30, Lexington, KY (US) 40502

( * ) Notice: Subject to any disclaimer, the term of this patent is extended or adjusted under 35 U.S.C. 154(b) by 0 days.

(21) Appl. No.: 11/282,864

(22) Filed: Nov. 19, 2005

Related U.S. Application Data

(60) Division of application No. 10/741,646, filed on Dec. 19, 2003, now abandoned, which is a continuation-in-part of application No. 10/453,002, filed on Jun. 3, 2003, now abandoned.

(60) Provisional application No. 60/385,082, filed on Jun. 3, 2002.

(51) Int. Cl.
*A61K 6/00* (2006.01)
*A61K 33/00* (2006.01)
*A61K 33/42* (2006.01)
*A61K 33/06* (2006.01)

(52) U.S. Cl. .................... 424/400; 424/600; 424/601; 424/682; 424/724

(58) Field of Classification Search ................ 424/400, 424/600, 601, 682, 724
See application file for complete search history.

(56) References Cited

U.S. PATENT DOCUMENTS 5,082,808 A * 1/1992 Nonami et al. ............. 501/95.3
5,968,253 A * 10/1999 Poser et al. ................. 106/691
6,511,510 B1 * 1/2003 de Bruijn et al. ......... 623/23.56

FOREIGN PATENT DOCUMENTS

WO     WO 97/40137     * 10/1997

OTHER PUBLICATIONS

Knabe et al., "Morphological evaluation of osteoblasts cultured on different calcium phosphate ceramics", Biomaterials, 1997, pp. 1339-1347, vol. 18, Elssevier Science Limited, Great Britain.

* cited by examiner

*Primary Examiner*—Johann Richter
*Assistant Examiner*—Konata M. George
(74) *Attorney, Agent, or Firm*—Stites & Harbison PLLC; John E. Vanderburgh

(57) ABSTRACT

A resorbable silica-calcium phosphate bioactive composite that finds utility for drug delivery. The bioactive composite is loaded with a pharmaceutical composition and releases a therapeutically effective amount of a pharmaceutical composition for periods of up the 28 days.

15 Claims, 3 Drawing Sheets

Treatment Temperature of the Ceramic

SILICA-CALCIUM PHOSPHATE BIOACTIVE COMPOSITE FOR IMPROVED SYNTHETIC GRAFT RESORBABILITY AND TISSUE REGENERATION

This application is a division of application Ser. No. 10/741,646 filed Dec. 19, 2003 now abandoned which is a continuation-in-part of application Ser. No. 10/453,002, filed Jun. 3, 2003 now abandoned claiming the benefit of the filing date of provisional application Ser. No. 60/385,082, filed Jun. 3, 2002 entitled SILICA-CALCIUM PHOSPHATE COMPOSITE FOR IMPROVED SYNTHETIC GRAFTED RESORBABILITY AND TISSUE REGENERATION, which are incorporated by reference herein.

FIELD OF THE INVENTION

This invention relates to the administration of pharmaceuticals and more particularly to a method and sustained release composition for the administration of a pharmaceutical directly at the site of a bone defect.

BACKGROUND OF THE INVENTION

Silica-based bioactive glasses and calcium phosphate ceramics have long been known to serve as synthetic materials useful in the promotion of bone formation in repairing bone fractures and the like. These materials are considered bioactive because they bond to bone and enhance bone tissue formation with a variable degree of success.

An estimated 11 million people in the United States have at least one medical device implant. Two types of implants, fixation devices (usually fracture fixation) and artificial joints are used in orthopedic treatments and oral and maxillofacial procedures. Approximately 80% of the fracture fixation requires adjuvant grafting. Among the joint replacement procedures an increasing number are revision surgeries with their adjuvant need for bone grafting.

Current approaches to difficult bone repair problems include utilization of autografts, allografts and synthetic grafts. Although at present auto graft material is preferentially used, there is limitation in its use, including donor site morbidity, limited donor bone supply, anatomical and structural problems and elevated levels of resorption during healing. The use of allografts has a disadvantage of eliciting an immunological response due to genetic differences and the risk of reducing transmissible diseases. Considerable attention has been directed to the use of synthetic materials for bone graft, most notably hydroxyapatite, tricalcium phosphate and bioactive glass. The synthetic graft material is also used to form coatings on implants, such as pins and the like, to promote attachment of new bone growth to the implement. In addition, these materials are also used as fillers in biopolymer composites and drug delivery vehicles.

SUMMARY OF THE INVENTION

In accordance with the present invention, there is provided a new resorbable silica-calcium phosphate bioactive composite (SCPC) that finds utility as a sustained release composition for the release of a pharmaceutical composition over a sustained period of time. As used herein the term "pharmaceutical composition includes any drug, peptide, anti-microbial peptide, enzyme and other growth factors that are used in the treatment, or prevention of disease or as a component of a medication. The composite can be mixed with other materials such as resins, bioglass, ceramics and the like to improve the physical properties of the delivery system.

More particularly, the SCPC is effective in the treatment of various diseases associated with bone reconstruction, such as osteomyelities, by application of the composite carrying a pharmaceutical composition directly in the bone tissue engineering scaffold to provide maintenance of a localized source of the drug and to facilitate bone tissue development and delivery of the drug over a period of time. Several drugs that are used for treatment of diseases can not be administered through the gastrointestinal tract due to their poor physicochemical properties or due to a high first-pass metabolism in the liver or degradation in the acidic atmosphere of the stomach. Digestive enzymes in the intestine or enzymes in the gut wall are responsible for the pre-systemic degradation of many drugs. Conventional administration of such drugs by repetitive injections is inconvenient and causes fluctuation of the blood drug level. In cases of trauma associated with bone loss, one major complication besides the need for bone reconstruction is the development of osteomyetities promoted by bacterial and fungal infection. About of 30% of the cases reported are treated with conventional therapy. Conventional treatment involves the repeated surgical removal of dead bone tissue coupled with repeated irrigation of the wound and prolonged systemic administration of antibiotics. Despite this aggressive approach, amputation is not an uncommon final solution particularly because the therapeutic efficiency of administrated drugs is strongly restricted due to the limited blood flow to the skeletal tissue. As a consequence, the development of more efficient therapy becomes very important.

The improved SCPC contains a relatively high concentration of silica and defines a surface that can contain four different phases; 1) silica modified with calcium and/or phosphorous, 2) unmodified silica/silanol groups required to nucleate calcium phosphate precipitation, 3) calcium phosphate modified with silica and 4) unmodified calcium phosphate. These four different phases ensure the availability of a surface with superior bioactivity as compared to calcium phosphate ceramic or bioactive glass conventionally used as a scaffold to promote bone tissue growth. In addition the presence of sodium in the form of $\beta$-$NaCaPO_4$ has a synergistic effect on the absorbability of protein that contributes to improved bioactivity.

While the resorption and bioactivity of bioactive glass is limited by the diffusion of Ca and P ions from the glass bulk to the surface, the resorption and bioactivity of the SCPC does not depend on the bulk composition. In addition to providing an immediate bioactive surface layer that enhances protein adsorption and cell function, the silicon released from the surface may have a stimulatory effect on bone cell function.

The bioactivity and the resorbability of the SCPC is affected and controlled by its chemical composition, its crystalline structure, the degree of the alkaline environment presented by the SCPC, its porosity and its thermal treatment temperature. For example disruption of the crystalline structure of the bioactive phases caused by the exchange of silica in the calcium phosphate phase and the exchange of phosphate into the silica phase improves the bioactivity of the SCPC. Moreover, the corrosion rate and resorbability are enhanced by this ion exchange in the bioactive phases. Similarly the porosity of the SCPC, which can be controlled during its formation by particle size of the ingredients, the presence of a fugitive agent or a foaming agent, and/or the pressure applied when forming green shapes prior to sintering, improves bioactivity with increasing porosity. It is preferred that the size of the pores be less than 800 µm and it has been found that good results are achieved when pore size ranges from about 0.1 µm to 500 µm The presence of an alkaline environment, such as provided by the presence of sodium ions, has been found to increase the bioactivity of the SCPC. Likewise the sintering temperature effects a change in the bioactivity and resorbability of the SCPC.

In the SCPC that has high calcium phosphate content, the silica is present both in amorphous form and in crystalline form. The crystal form can comprise L-quartz and/or α-cristobalite (tetragonal crystal structure). The silica may be present in amounts ranging from 0.3094 moles to 0.9283 moles. The calcium phosphate portion of the SCPC can be present in many forms such as for example, hydroxyapatite, tricalcium phosphate, dibasic calcium phosphate, calcium pyrophosphate ($\beta$-$Ca_2P_2O_7$(H)) and/or $\beta$-$NaCaPO_4$ (rhenanite). The precise structure of the SCPC will depend on the initial chemical concentration of each component and on the thermal treatment protocol.

DESCRIPTION OF THE INVENTION

Figure 1:
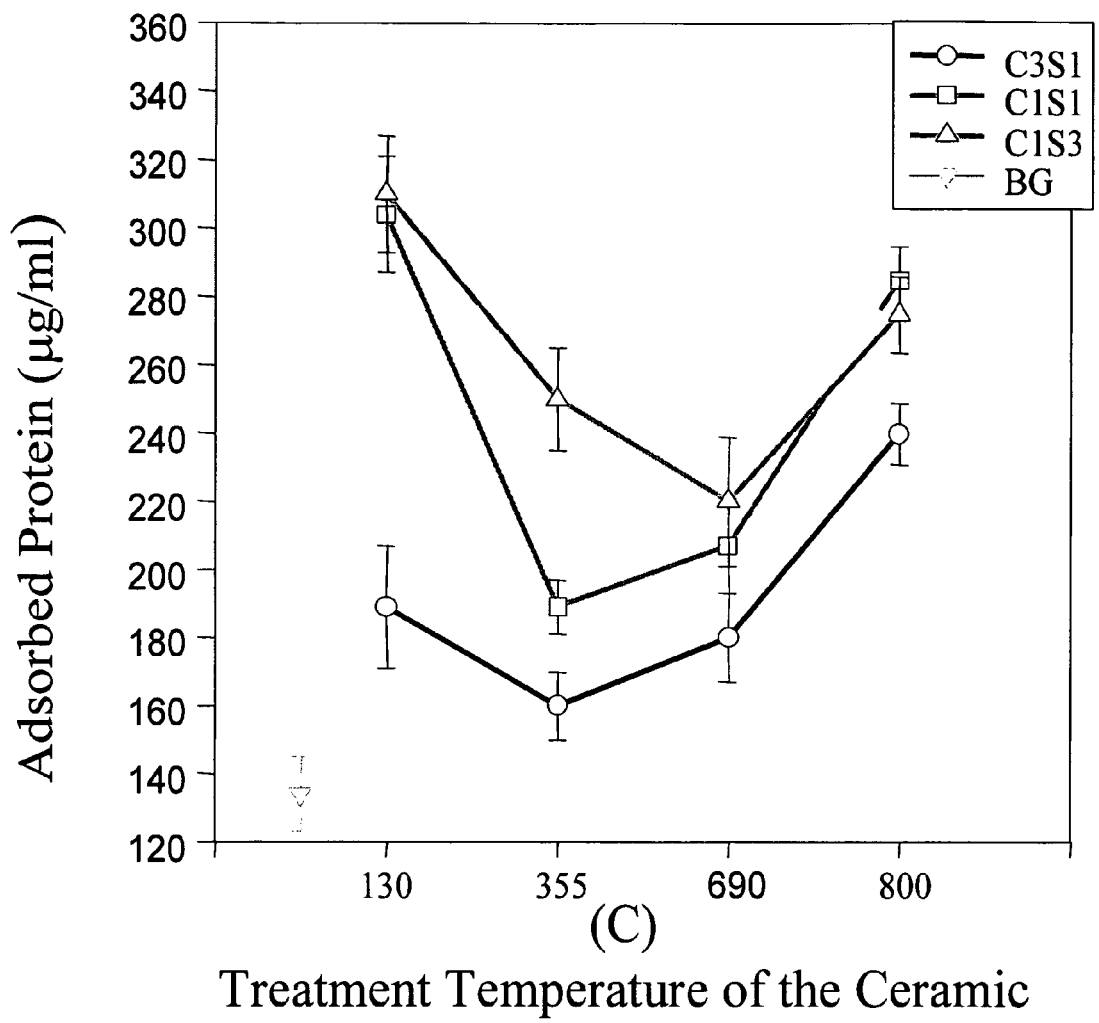
FIG. 1 is a plot of adsorbed protein versus the temperature treatment of several samples of composite made in accordance with the invention and conventional bioglass.

The SCPC is prepared by forming an aqueous or non-aqueous paste of an organic or inorganic silica salt equivalent to about 0.3 moles to about 0.9 mole of silica and a calcium phosphate. Preferably the silicate salt is sodium silicate although other silicate salts can be used, particularly with the inclusion of a sodium salt or sodium oxide to provide sodium ions to the composite. The calcium phosphate is preferably bicalcium phosphate. The paste may be pressed into pellets for more convenient handling. In the alternative, the sodium silicate and bicalcium phosphate may be mixed as a dry powder.

The mixture, be it in the form of pellets or other formed shape or as a dried powder, is sintered at temperatures ranging from 130° C. to 1200° C. Following thermal treatment, the SCPC material is ready for use such as by forming as granules or into a shape, such as a block, sphere or sheet or to form at least a portion of a suitable prosthesis for implant or direct application on bone being repaired. For example, the composite can be mixed with a ceramic, bio-resin or bioglass to enhance the physical properties of the delivery system. In addition, the delivery system can be deposited as a layer on a device such as a pin for insertion in the bone being repaired.

It is highly preferred that the bioactive composite be porous. Good results can be achieved when porosity ranges from 10 percent to as high as 80 percent by volume of the composite. For the higher porosities it is preferred to include a suitable pore former such as a fugitive material that is consumed during the thermal treatment process. Likewise, pore formation can be initiated in the raw composite mix by including a foaming agent or a fugitive solvent. Pore forming and fugitive agents for use in ceramic composites are well known and are commercially available and the selection of a suitable agent is clearly understood. In many cases the solvent of the composite paste will itself form pores in sufficient number and size as it leaves the paste during thermal treatment. It is preferred that the pores be less than 800 µm to aid in maintaining the structural integrity of the finished composite. The bioactive composite may have a pore size of between about 0.1 µm to about 500 µm and good results are achieved with pore sizes ranging from about 10 µm to about 300 µm The SCPC has been tested for adsorption of serum protein, a necessary first step to the production of new bone growth around the SCPC, and it was found that protein adsorption varied with the sintering temperature which the material was pretreated at during processing. It was found that protein adsorption dropped as the sintering temperature increased from 130° C. to about 690° C. and thereafter sharply increased between 690° C. and 800° C. Although it is not fully understood, this may be attributed to the transformation of silica from amorphous phase to a crystalline phase which may inhibit protein adsorption onto the surface of the SCPC pretreated in the temperature range 130-690° C., however, the silica is transformed from L-quartz into α-cristobalite (after thermal treatment above 690° C.) which is associated with a significant increase in serum protein adsorption. In addition, the formation of $\beta$-$NaCaPO_4$ which also begins forming at about 690° C. and increases as the treatment temperature increases above about 690° C. is also associated with a significant increase in serum protein adsorption. Regardless of the thermal treatment, however, the SCPC of the present invention absorbs more protein than the standard bioactive glass alone. Also, the disruption of the structure of the SCPC caused by the exchange of silica in the calcium phosphate phase and the exchange of phosphate into the silica phase improves protein adsorption.

Silica containing calcium phosphate composites (SCPCs) have been prepared as described above The SCPCs, identified as C3S1, C1S1 and C1S3 were sintered at temperatures ranging between 355° C. and 800° C. The phase compositions at several sintering temperatures have been determined and are set out in Table 1. The compositions were tested for protein absorption as reported by Ahmed, El-Ghannam and Fouda, biomaterials Forum, 27th Annual Meeting Transactions, 23, May-June 2001.

TABLE 1

| Sample | $SiO_2$ (Mole) | Temp (° C.) | Phase Composition |
|---|---|---|---|
| C3S1 | 0.3094 | 355 | L-quartz + $\beta$-$Ca_2P_2O_7$ + $\beta$-$Ca_3(PO_4)_2$ + B-$NaCaPO_4$ |
| C1S1 | 0.6193 | 355 | L-quartz + $\gamma$-$Ca_2P_2O_7$ + $\beta$-$Ca_3(PO_4)_2$ + B-$NaCaPO_4$ |
| C1S3 | 0.9283 | 355 | A-cristobalite + $\beta$-$NaCaPO_4$ |
| C3S1 | 0.3094 | 690 | A-cristobalite)[+] + $\beta$-$Ca_2P_2O_7$ + $\beta$-$NaCaPO_4$ |
| C1S1 | 0.6193 | 690 | A-cristobalite + $\beta$-$NaCaPO_4$ + L-Quartz |
| C1S3 | 0.9283 | 690 | A-cristobalite + $\beta$-$NaCaPO_4$ + $Na_2Si_3O_5$ |
| C3S1 | 0.3094 | 800 | A-cristobalite[+] + $\beta$-$Ca_2P_2O_7$ + $\beta$-$NaCaPO_4$ |
| C1S1 | 0.6193 | 800 | A-cristobalite + $\beta$-$NaCaPO_4$ + L-quartz |
| C1S3 | 0.9283 | 800 | A-cristobalite + $\beta$-$NaCaPO_4$ + L-quartz |

The composition of the samples after thermal treatment was determined by X-ray diffraction analysis and scanning electron microscopy. The shift in the 2θ in the position of the characteristic signals of the silica and calcium phosphate phases is indicative of the silicate-phosphate ion substitution. The ion substitution exchange resulted in significant decrease in the crystallization temperature in both the silica and calcium phosphate phases. The formation of these crystalline phases at lower temperature increased the bioactivity of the SCPC.

Particles (90-250 μm) from each of the samples were separately immersed in a simulated body fluid comprising fetal bovine serum for 3 hours at 37° C. After immersion the protein was extracted using 1% SDS. Protein concentration was determined using a gold staining dot block technique. For a comparison, a control experiment using bioactive glass particles of the same particle size range was run in parallel. The results are set forth in FIG. 1 where the X-axis represents the temperature at which the ceramic was pretreated at during sintering. After the samples were cooled down to room temperature they were immersed in protein solution. The adsorbed protein was determined as described above. Samples containing a-cristobalite and β-NaCaPO$_4$ adsorbed statistically significant higher amounts of serum protein than samples containing L-quartz and pyrophosphate. As the amount of the cristobalite increased the adsorption of protein increased.

The composition of the present invention, particularly the C1S3 material, has a strong stimulatory effect on stem cell differentiation into osteoblasts and can be used as a delivery system for mesenchymal stem cells.

The following examples illustrate the system for delivery of an antibiotic. It should be understood that the delivery system is not so limited and will be used for the delivery of any drug molecule, peptides, enzymes and other growth factors for the treatment and prevention of disease.

EXAMPLE 1

One approach to increase the efficiency of bone disease treatment is the use of sustained release systems that include drug supports in synthetic and natural materials. The advantage of a sustained release system of antibiotic in the treatment of osteomyelities is the maintenance of a localized increase of the drug and thus a more effective control of bacterial and fungal growth. Other potential advantages include drug targeting, improved compliance and comfort.

Vancomycin hydrochloride (Vancocine®) solution of 8 mg/ml was prepared in Tris buffer solution (pH 7.21). One milliliter of the drug solution was micropipetted on 0.2 g SCPC particles (C1S3 and C3S1) of grain size 300-425 μm in 20 ml glass vials. The particles were immersed in the drug solution and incubated at 37° C. for 24 hours. The particles were then removed, washed with 1 ml Tris buffer solution (pH 7.21) for 30 sec and dried at 37° C. overnight. For comparison, control samples (C3S1 and C1S3) were immersed in drug-free solution and run in parallel. All samples were performed in triplicates.

To evaluate the kinetics of drug release from the SCPC, the SCPC particles loaded with the drug were immersed in 12 ml of simulated body fluid (SBF), as described in Example 1, and incubated at 370 C. The SBF volume (12 ml) was selected such that its pH does not change during immersion. 2 ml of the SBF were withdrawn and replaced by another fresh 2 ml SBF after 1, 3, 6, 24, and 48 h. At 72 h, 50% of the SBF were replaced day to day up to 4 weeks.

The concentration of vancomycin hydrochloride released from the SCPC into the SBF was calculated by measuring the absorbance of vancomycin hydrochloride at 280 nm using a spectrophotometer. The eluted SBF solution samples were frozen at −4° C. for the microbiological assay.

The mean cumulative release of vancomycin hydrochloride as a function of elution time for C1S3 showed drug release at nearly constant rate for 6 h after immersion followed by first-order release up to 3 days. The average release rate over the entire first-order stage is 33.19699 μg/h. Later, a slower release stage takes place with an average release rate of 1.2 μg/h for the time period 3-28 day. The average release rate from 5-28 day is 1.3

Figure 2:
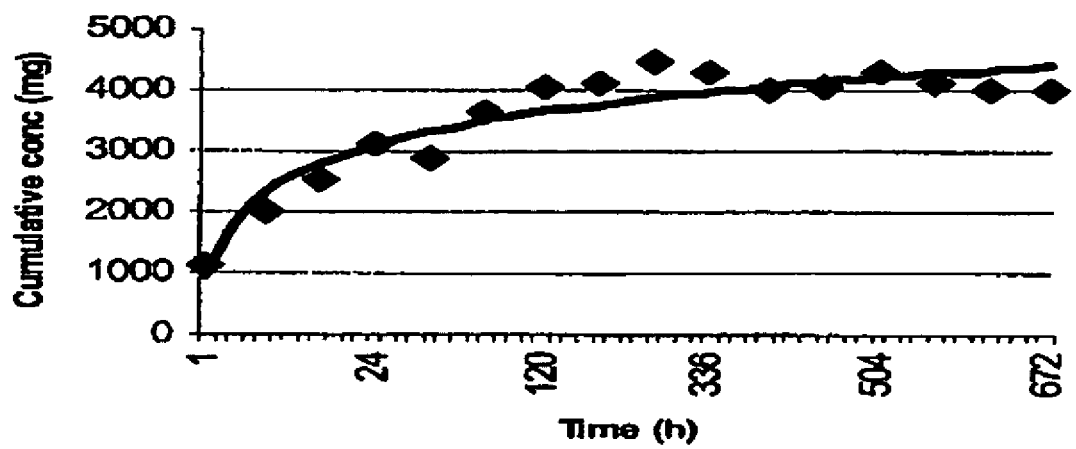
FIG. 2 is a plot of the cumulative concentration of vancomycin hydrochloride against time of release.

The C1S3 composite showed sustained release of an effective dose of vancomycin hydrochloride over a period of 672 hours (28 days). A biphasic release kinetic is observed; a first-order release followed by a zero order release. The transition from first-order to zero-order release occurred at the interval from day 1-9. The average release rate over the first order regions in the ranges 3-24 h and 24-120 h, 5-9 days are 46.28531 and 11.50703, and 4.24778 μg/h respectively. The average release rate in the time interval 1-28 days was 2.18 μg/h. A plot of the results appears in FIG. 2 which is a plot of the cumulative concentration of the vancomycin hydrochloride released over a period expressed as hours.

The controlled release profile of vancomycin hydrochloride (fast initial release followed by a slower long term release of effective dose up to day 28) indicates that the C1S3 composite exhibits utility as a carrier for antibiotics to treat bone infections. The beneficial two-stage release was observed for all composites (C1S3, C1S1 and C3S1) and makes the composite material superior to other antibiotic-loaded ceramics characterized by a burst release that is usually observed.

Bioactivity of the Released Vancomycin Hydrochloride

The average release rate of vancomycin hydrochloride released during the 28 days immersion in simulated body fluid exceeds the minimum inhibitory concentration for most pathogens commonly isolated in orthopedic infections. The minimum inhibitory concentration, minimum bactericidal concentrations, and breakpoint sensitivity of vancomycin hydrochloride for *Staphylococcus aureus* were 1.18, 2.34, and 5 mg/L respectively.

EXAMPLE 2

The bioactivity of the vancomycin hydrochloride released from C1S3 was determined using standard disk susceptibility protocol. The disk-susceptibility protocol includes inoculation of agar plate with bacteria (*Staphylococcus aureus*).

Paper disks (6 mm in diameter) were impregnated separately in the solutions which contain the drug released from the delivery systems of Example 1 above after different release time intervals. The impregnated disks were placed separately on the agar plate inoculated with bacteria and the inhibition zone around the disc was measured as a function of time. In addition, the relative activity of the antibiotic released from the composite was calculated using the equation: The relative activity was reported as: Relative activity= (diameter of the sample inhibition zone/maximum inhibition zone)×100

Figure 3:
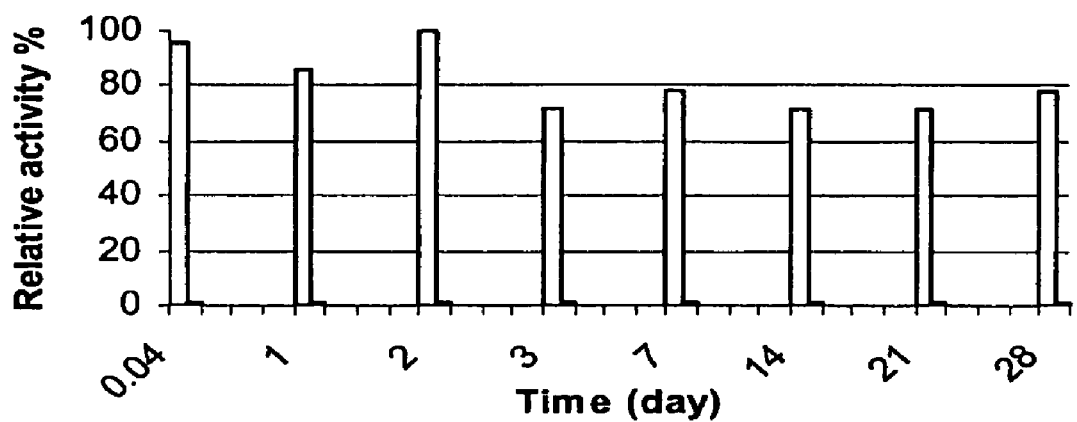
FIG. 3 is a bar graph showing the relative activity of vancomycin hydrochloride at various release times.

The results, summarized in FIG. 3, indicate an average relative activity of the antibiotic over the 28 day test period to be in excess of about 80%.

The foregoing examples are by way illustration only and should not be taken as limiting the invention. Although preferred embodiments have been described herein in detail, it is understood by those skilled in the art that variations may be made thereto without departing from the scope of the invention as defined by the claims appended hereto.

I claim:

1. A delivery system for pharmaceutical compositions comprising a resorbable silica-calcium phosphate bioactive composite and a therapeutically effective amount of a pharmaceutical composition, said system comprising the equivalent of between about 0.3 moles to about 0.9 mole of silica, said therapeutically effective amount of a pharmaceutical composition being absorbed by said composite and released over a period of time.

2. The delivery system of claim 1 wherein resorbable silica-calcium phosphate bioactive composite is thermally treated at temperatures of between about 355° C. to about 800° C. prior to loading said pharmaceutical composition.

3. The delivery system of claim 1 wherein resorbable silica-calcium phosphate bioactive composite has a porosity of between about 10% to about 80%.

4. The delivery system of claim 1 wherein resorbable silica-calcium phosphate bioactive composite has a pore size of less than 800 μm.

5. The delivery system of claim 4 wherein resorbable silica-calcium phosphate bioactive composite has a pore size of between about 0.1 μm and about 500 μm.

6. The delivery system of claim 1 wherein said pharmaceutical composition is vancomycin hydrochloride.

7. The delivery system of claim 1 comprising a therapeutically effective amount of said pharmaceutical composition loaded on particles of said resorbable silica-calcium phosphate bioactive composite.

8. The delivery system of claim 7 wherein said particles of said resorbable silica-calcium phosphate bioactive composite have a grain size 300-425 μm.

9. The delivery system of claim 1 wherein a therapeutically effective amount of said pharmaceutical composition is released from said resorbable silica-calcium phosphate bioactive composite over a period of up to about 28 days.

10. The delivery system of claim 9 wherein said pharmaceutical composition is released in two stages, a first stage of increasing cumulative amounts being released occurring over a period of between about 5 days to about 9 days and a second stage of maintaining a relatively uniform cumulative amount occurring from about 5 days to about 9 days to about 28 days.

11. The delivery system of claim 6 for the treatment of bone infections.

12. The delivery system of claim 1 wherein said pharmaceutical composition comprises mesenchymal stem cells.

13. A method for the production of a delivery system for pharmaceutical compositions comprising the steps of:
   a. forming an aqueous or non-aqueous paste of an organic or inorganic silica salt equivalent to about 0.3 moles to about 0.9 mole of silica and a calcium phosphate;
   b. sintering said mixture at temperatures ranging from about 355° C. to about 800° C. to form a composite;
   c. contacting sintered particles of said composite with solution of a pharmaceutical agent to cause a therapeutic amount of said agent to be absorbed by said particles of said composite; and
   d. incubating particles of composite.

14. The method of claim 13 wherein said mixture is sintered at a temperature of between about 600° C. and about 800° C.

15. The method of claim 13 wherein said particles of said composite are contacted by a solution of an antibiotic in tris buffer solution.

* * * * *

UNITED STATES PATENT AND TRADEMARK OFFICE
CERTIFICATE OF CORRECTION

| | | |
|---|---|---|
| PATENT NO. | : 7,223,414 B1 | Page 1 of 1 |
| APPLICATION NO. | : 11/282864 | |
| DATED | : May 29, 2007 | |
| INVENTOR(S) | : El-Ghannam | |

It is certified that error appears in the above-identified patent and that said Letters Patent is hereby corrected as shown below:

IN THE CLAIMS:

Claim 10, col. 8, line 6: Delete "to about 9 days"

Signed and Sealed this

Thirty-first Day of July, 2007

JON W. DUDAS
*Director of the United States Patent and Trademark Office*